United States Patent [19]
Swedberg et al.

[11] Patent Number: 5,871,457
[45] Date of Patent: Feb. 16, 1999

[54] KNEE POSITIONING SUPPORT

[75] Inventors: Lynn M. Swedberg, Spokane, Wash.; Karen A. Fula, Milwaukee, Wis.

[73] Assignee: Smith & Nephrew, Inc., Memphis, Tenn.

[21] Appl. No.: 995,026

[22] Filed: Dec. 19, 1997

[51] Int. Cl.$^6$ ........................................................ A61F 5/00
[52] U.S. Cl. ................................. 602/24; 5/640; 128/845; 606/240
[58] Field of Search ................................. 602/12, 23, 24; 128/845, 878, 882; 5/620, 621, 623, 624, 630, 632, 640, 643; 606/240

[56] References Cited

U.S. PATENT DOCUMENTS

| | | | |
|---|---|---|---|
| D. 342,856 | 1/1994 | Hagen | ........................................ 5/648 |
| D. 345,668 | 4/1994 | Braly . | |
| 3,931,654 | 1/1976 | Spann . | |
| 4,177,806 | 12/1979 | Griffin . | |
| 4,706,302 | 11/1987 | Padfield et al. . | |
| 4,730,801 | 3/1988 | Clowars | ................................... 5/648 X |
| 4,736,477 | 4/1988 | Moore . | |
| 4,777,678 | 10/1988 | Moore | ..................................... 5/648 X |
| 4,805,605 | 2/1989 | Glassman . | |
| 4,840,362 | 6/1989 | Bremer et al. | ........................... 5/648 X |
| 4,889,109 | 12/1989 | Gifford . | |
| 4,910,818 | 3/1990 | Grabill et al. . | |
| 4,970,742 | 11/1990 | Keener | ................................... 5/648 X |
| 5,125,123 | 6/1992 | Engle | ......................................... 5/648 |
| 5,134,739 | 8/1992 | Gaffe et al. . | |
| 5,279,310 | 1/1994 | Hsien | ...................................... 128/845 |
| 5,289,828 | 3/1994 | Toth . | |
| 5,626,616 | 5/1997 | Speece | .................................. 128/845 X |
| 5,725,486 | 3/1998 | Engelman | ................................... 602/5 |
| 5,771,512 | 6/1998 | Kurakake et al. | ........................... 5/623 |

*Primary Examiner*—Linda C.M. Dvorak

[57] ABSTRACT

A modular knee positioning support comprising at least one leg-engaging portion removably attached to a center wedge portion. The leg-engaging portion has a flat bottom with a single angled edge, and a top concave portion for receiving the upper and lower portions of a leg. The support can be made of a carvable foam. The foam can be covered with a washable cloth.

21 Claims, 8 Drawing Sheets

KNEE POSITIONING SUPPORT

SPECIFICATION

CROSS-REFERENCE TO RELATED APPLICATIONS

Not applicable.

STATEMENT REGARDING FEDERALLY SPONSORED RESEARCH

Not applicable.

BACKGROUND OF THE INVENTION

1. Field of the Invention

The present invention relates to orthopedic devices and devices used in the rehabilitation of neurological patients with contracture. In particular, the invention relates to supports and more specifically to an improved foam knee support wherein the knee support is modular, adjustable, and can be used with either one leg to two.

The knee positioning support is comprised of at least one leg-engaging trough portion and can include at least one additional wedge portion which can be attached to either side of the leg-engaging trough portion. The use of two leg-engaging portions attached to opposite sides of a center wedge portion provides a knee positioning support that can accommodate two legs. Because the angle of attachment of the leg-engaging troughs to the wedge portion is adjustable, the two legs can be positioned at a variety of different angles. In addition, the flat bottom surface of the leg-engaging trough has one angled edge which allows the use of the support in either a back-lying or side-lying position. If a side-lying position is desired to be prevented, a wedge portion can be attached to the side of the leg-engaging trough portion that is integrally connected to the angled edge of the bottom of the leg-engaging trough portion. Furthermore, the invention support can be constructed from carvable foam to provide a custom fit, and to accommodate people who do not have symmetrical flexion of the knees.

2. Description of the Related Art

It is often necessary to specifically position the legs of persons with mild to moderate spasticity, arthritis, and contractures, particularly those recovering from strokes, traumatic brain injuries, dementia and other neurological impairments, and persons with lower extremity amputations for extended periods. Specific positioning of the legs helps to flex the hips and knees so as to relieve stress on the lower back and/or maintain the legs in a fixed position. Specific positioning of the knees of such persons also helps prevent further contracture and helps to maintain their current range of leg motion. Patients with severe spasticity, for example patients suffering from cerebral palsy, head trauma, or stroke, often experience a scissors gate; their knees that tend to cross and push into one another. For such patients it is desirable to separate the legs to prevent contracture, and to inhibit the development of further abnormal muscle tone or to position patients that have reduced or minimal muscle strength and mobility.

In addition, these conditions are uncomfortable for the patient, often causing pressure sores due to the bony prominences of the legs in prolonged contact, prolonged skin-on-skin contact, and even prolonged skin on bed-sheet contact due to extensive bed rest.

Certain prior art devices, such as the knee separation cushion described in U.S. Pat. No. 4,889,109 provide a leg cushion with simultaneously supports the legs of a supine wearer in a bent at the knee position, while maintaining a cushion between the knees of said wearer. However, such a prior art device is useful only when both knees are affected. If only one knee is affected, the unaffected leg is still subjected to the fixed positioning. Similarly, U.S. Pat. No. 4,910,818 describes a leg positioning assembly that includes a pillow adapted to separate the knees of a patient and to maintain the knee in flexion. Again, however, this device is useful only for people who wish to maintain a fixed position of both knees relative to each other. It is not particularly helpful for maintaining a single knee in flexion. In addition, both of these prior art devices maintain the hip flexion angle at a fixed position as the position of the knee support device relative to the hip is not adjustable.

U.S. Pat. No. 5,134,739 and U.S. Pat. No. 3,946,451 both provide a device for giving a set position to the lower limbs of persons required to remain in a supine position for an extended period. These devices comprise at least one block offering two side support surfaces for the legs, the vertical plans of the two surfaces converging at a determined angle corresponding to the desired positioning of the two lower limbs. However, unlike the modular knee support of the instant invention, these prior art devices are unsuitable for side-lying persons. The bottom surface of the leg-receiving portion of these prior art devices have two flat edges making it impossible for side-lying persons to comfortably rest their legs and maintain the desired flexion angle position. Furthermore, the side surfaces of the central block of the U.S. Pat. No. 5,134,739 device converges toward the patient and diverges toward the feet further limiting the number of positions the legs and/or hips of the patients can be adjusted.

U.S. Pat. No. 5,289,828 describes a device that allows patients to be in a back-lying or side-lying position. However, this device does not allow the flexion angle of the knee to be variably adjusted. Indeed, the wedge-type device of the 5,289,828 patent does not allow for bending of the knee at all. In addition, only a single leg can be maintained in a specific elevated fixed position by the device of the 5,289,828 patent at one time. Similarly, U.S. Pat. No. 4,392,489 also describes a wedge-like device that does not allow for bending of the knee and requires both legs to be immobilized at once.

None of these prior art knee support devices can provide either a back-lying or side-lying patient the ability to accommodate a variety of flexion angles for either one or both legs while maintaining either one or both knee flexion angles in a fixed, bent position.

SUMMARY OF THE INVENTION

The present invention solves the problems of these prior art devices by providing a knee positioning support that is modular, adjustable, and can be used with either one leg to two. One or two legs can be positioned at a variety of different angles while the patient is in a back-lying or side-lying position. Furthermore, the invention support can be constructed from carvable foam to provide a custom fit, to accommodate people who do not have symmetrical flexion of the knees or hips, to prevent further loss of extension, and can help prevent pressure and bed sores that can be caused by prolonged contact of skin on skin, skin on sheets, and the abnormal or prolonged interaction of the bony prominences of the legs.

The invention knee positioning support includes a removable attachable leg-engaging trough portion. This leg-engaging trough portion has a flat bottom surface, a concave top surface and two sides. The flat bottom surface of the leg-engaging portion has two edges, a straight first edge, and an angled second edge. The flat bottom surface maintains the knee in the correct position when the person is back-lying while the angled second edge of the bottom surface helps maintain the correct position when the person is side-lying.

The straight first edge of the bottom surface is integrally connected with the first side of the leg-engaging portion. The angled second edge of the bottom surface is integrally connected to the second side of the leg-engaging portion. The concave top (trough) surface is adapted to engage the upper and lower portions of a leg in a relatively comfortable, but immobile manner.

In one embodiment, the leg-engaging portion is used by itself. A person's leg is placed within the concave portion of the top surface of the leg-engaging portion.

In another embodiment, the leg-engaging portion is attached to a first side or second side of a wedge portion at the first side of the leg-engaging portion. The wedge portion shown has an irregular pentagonal shape, a flat bottom surface with straight first and second edges, a first and second side, and a top surface. The top, generally convex surface of the wedge portion can be taller in height than the top concave surface of the leg-engaging portion. The attachment of the leg-engaging portion to the wedge can be varied to accommodate a variety of different hip flexion angles.

In yet another embodiment, two leg-engaging portions are used. The first side of a first leg-engaging portion is attached to a first side of a wedge portion, and the first side of a second leg-engaging portion is attached to the wedge portion at the second side of the wedge portion. The angle of attachment of both leg-engaging portions to the center wedge portion can be adjusted to accommodate a variety of different hip flexion angles. Thus, the adjustability of the two leg-engaging portions relative to the center wedge and relative to each other provide the invention knee support with the ability to accommodate people who do not have, or do not require, symmetrical flexion of the knees.

The modular nature of this invention device allows all possible combinations of leg-engaging trough portions and wedge portions depending on what is desired for a particular patient at a particular time. For example, to increase the separation of the legs, more than one center wedge portion can be positioned between one or two leg-engaging trough portions. Where it is preferable that a patient be prevented from side-lying, a leg-engaging portion can be attached to a wedge portion at the second side of the leg-engaging portion. Because the second side of the leg-engaging portion is integrally connected to the angled edge of the bottom surface of the leg-engaging portion, this type of a wedge attachment prevents a back-lying patient from rolling over to the side. In addition, straps can be used to help maintain the leg in the invention support device during, for example, sleep.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF INVENTION

Due to the modular nature of the invention device, a variety of different embodiments exist. The use of any specific embodiment will depend on a patient's needs at a particular time. Furthermore, because the invention device is made from a carvable foam, the size and angle of each of the modular pieces can vary. This is a great advantage in that it not only provides the ability to change the size of the device to accommodate smaller or larger patients, it provides the ability to change the specific knee flexion angle at which the patient's leg will be supported. Thus, patients who cannot fit in traditional supports because of too little or too much flexion can fit in this device by simply adding or removing specific pieces of the carvable foam to accommodate their specific needs. Because a patient's needs often change as the result of, for example, treatment, different sections, and different sized sections, can be used at different times to achieve the desired flexion or extension. Again, the size and shape of the particular modular pieces can vary between patients, and can vary at different times with a single patient.

The invention device consists of essentially two different types of modular components; a leg-engaging trough portion, and a wedge portion (FIGS. 1–4). The leg-engaging portion 20 has a bottom surface 12, and a top concave trough-shaped surface 14, a first side 16, a second side 18, a front surface 17, and a back surface 19 (see also FIGS. 8, and 9). The bottom surface 12 of the leg-engaging portion 20 is flat and has two edges, a straight first edge 22, and an angled second edge 24. The straight first edge 22 of the bottom surface 12 is integrally connected with the first side 16 of the leg-engaging portion 20. The angled second edge 24 of the bottom surface 12 is integrally connected to the second side 18 of the leg-engaging portion 20. The top surface 14 is concave, trough-shaped and adapted to engage the upper and lower portions of a leg (L1).

Figure 8:
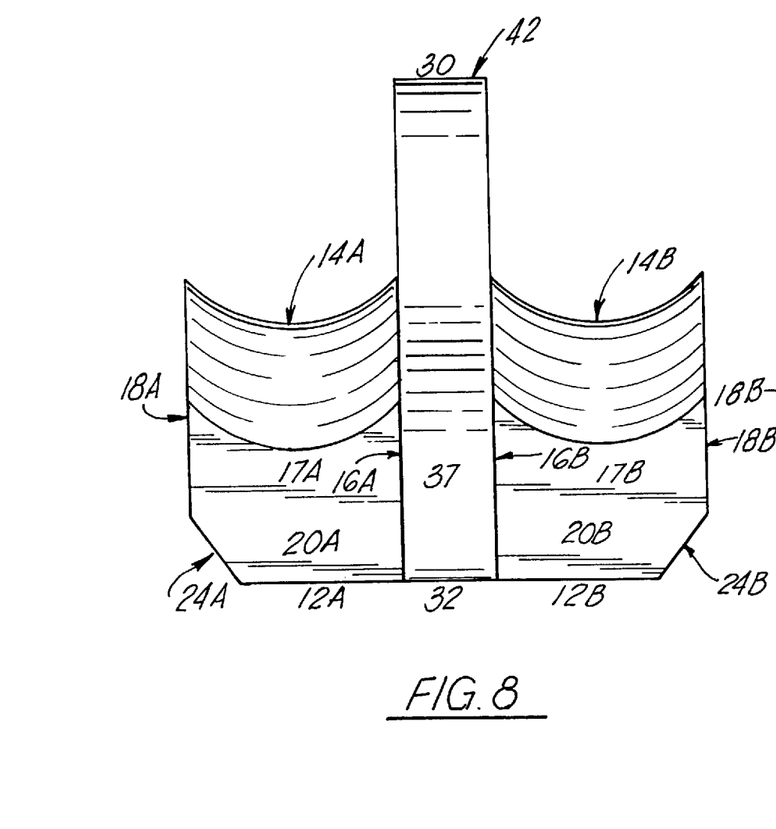
FIG. 8 shows a front perspective view of the assembled invention.
Figure 9:
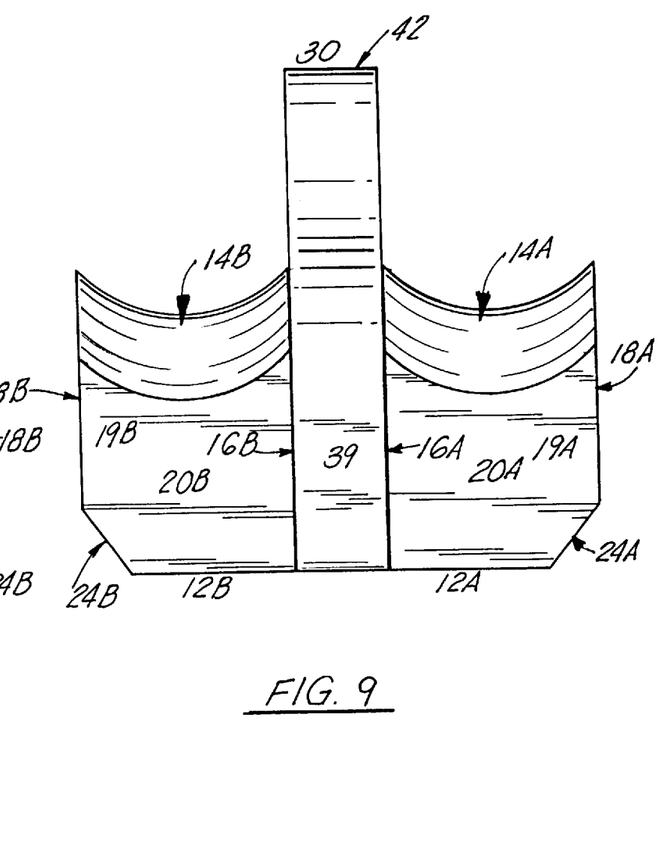
FIG. 9 shows a back perspective view of the assembled invention.

The wedge portion 30 has a flat bottom surface 32, a first side 38, second side 40, a top surface 42, a front surface 37, and a back surface 39 (see also FIGS. 8, and 9). The irregular pentagonal wedge portion 30 can be angled upwards toward the hips of the patient (see FIGS. 12, and 13). However, the angle, shape and size of the wedge portion 30 can be changed to suit the different needs of different patients, or the same patient at different times. The wedge portion 30 acts to distribute the pressure of one leg against the other to help prevent pressure sores caused by prolonged skin on skin contact or prolonged contact of the bony prominences of the legs.

Figure 1:
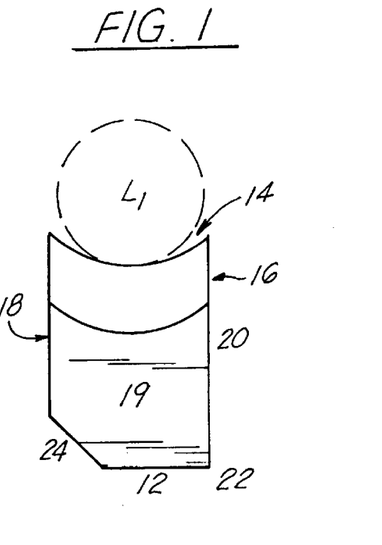
FIG. 1 shows a perspective view of the leg-engaging trough portion of the instant invention.

FIG. 1 shows one preferred embodiment wherein of the leg-engaging portion is used by itself. In this embodiment, the patient's leg L1, is positioned within the trough-shaped concave top surface 14, of the leg-engaging portion 20. The foam support provides comfortable, yet firm positioning of the knee of the patient in a desired flexion angle.

Figure 2:
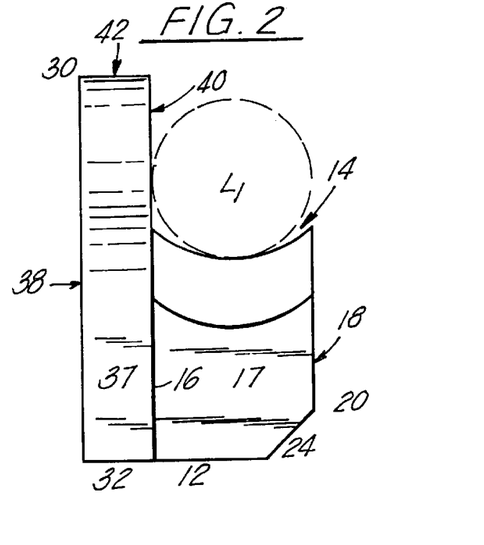
FIG. 2 shows a perspective view of one alternative embodiment of the assembled invention where one wedge portion is reversibly connected to one side of a leg-engaging portion.
Figure 3:
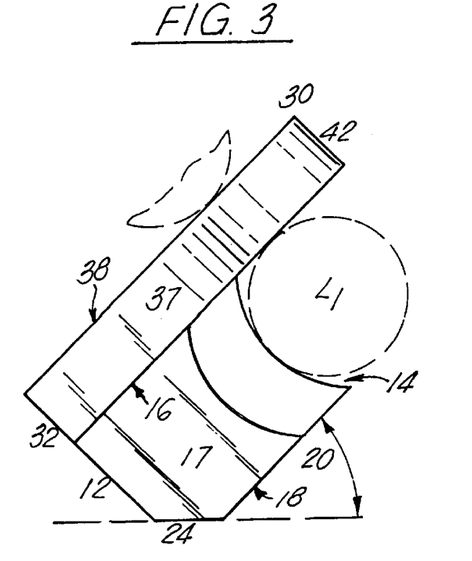
FIG. 3 shows a perspective view of the embodiment of FIG. 2 when the patient is side-lying.

An alternative embodiment, shown in FIG. 2, uses a single wedge portion 30 in addition to the single leg-engaging portion 20. The single wedge portion 30 distributes the pressure of one leg against the other to help prevent pressure sores caused by prolonged skin on skin contact or prolonged contact of the bony prominences of the legs. In both of these embodiments, the person can be either back-lying or side-lying. As shown in FIG. 3, when the person is side-lying, the angled second edge 24 of the bottom surface 12 helps maintain the correct position.

Figure 4:
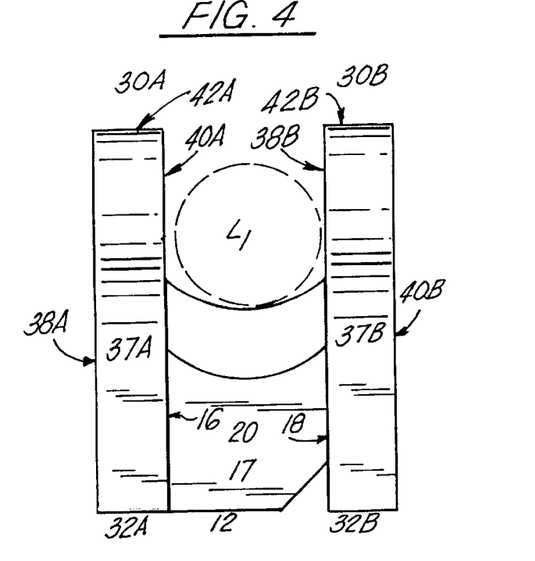
FIG. 4 shows an alternative embodiment of the instant invention in which two wedge portions are attached to opposite sides of a single leg-engaging portion.

The leg-engaging portion 20 can also be attached to a wedge portion 30 at the second side 18 of the leg-engaging portion (see, FIG. 4). Because the second side 18 of the leg-engaging portion 20 is integrally connected to the angled edge 24 of the leg-engaging portion 20, the attachment of the wedge to this side 18 prevents a patient from side-lying. While FIG. 4 shows the use of two wedge portions 30A and 30B, it is also possible to prevent side-lying with a single wedge portion 30 connected to the second side 18 of a single leg-engaging portion 20.

Figures 5A, 5B, 5C, 5D, 5E:
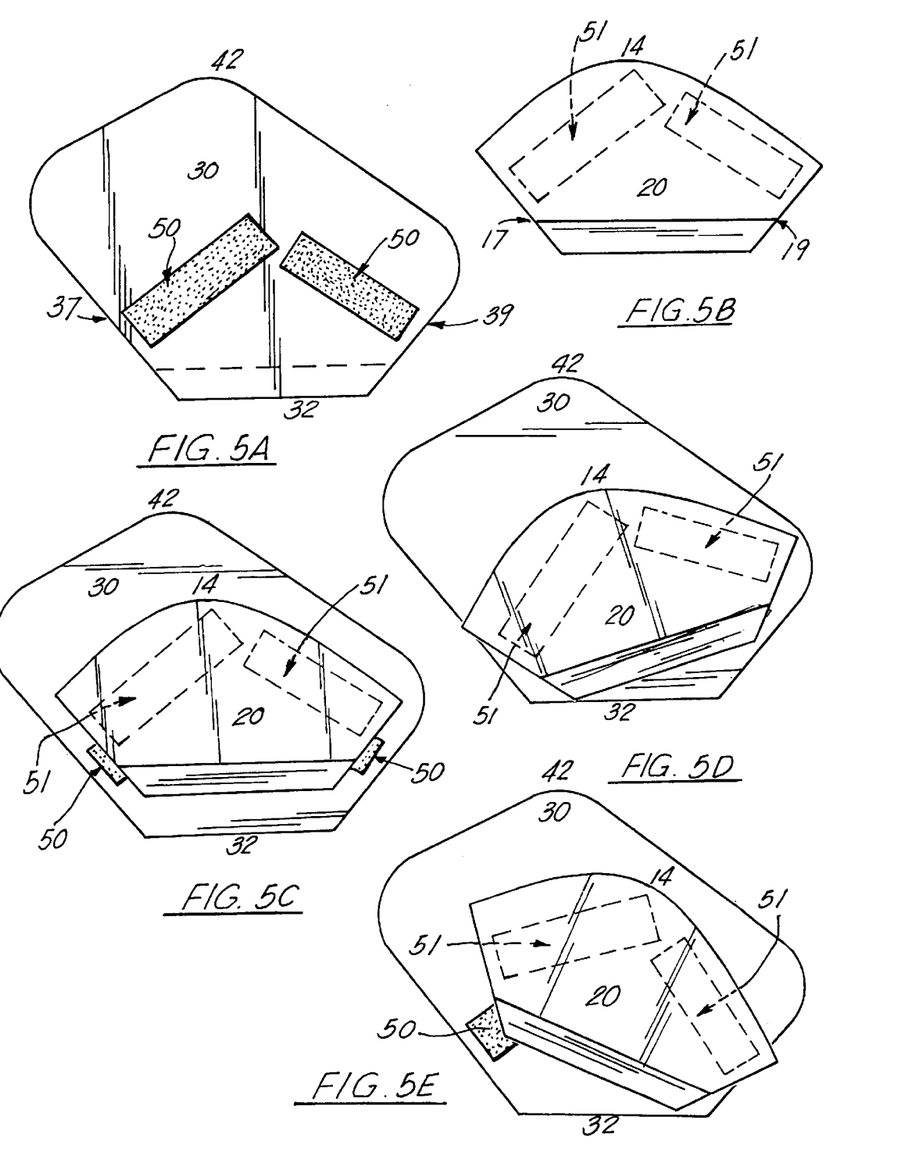
FIGS. 5A–E shows a side plan view of one embodiment of the instant invention illustrating the various placement possibilities of the component pieces relative to each other.

The modular components 20 and 30 of the instant invention are reversibly attachable to each other in a variety of positions. Such attachments form the basis for the modular nature of the invention support. An example of a means by which such a reversible, adjustable attachment can be made is via hook and loop material (50, and 51) (see FIGS. 5A–E), such as Velcro® strips. FIG. 5A shows the reversible, adjustable attachment material 50 on one side of a wedge portion 30. FIG. 5B shows the compatible, mateable material 51 on a leg-engaging portion 20. FIGS. 5C–5E show different possible alignments of the leg-engaging portion 20 on the wedge portion 30 via the reversible, adjustable, attachment material 50, and 51. As can be seen, the angle of the leg-engaging portion can be adjusted to accommodate different desired flexion angles for the patient.

All of the above mentioned embodiments are useful when it is desirable to position a single leg in a desired flexion angle using a foam support. However, due to the modular nature of the invention device, it is also possible to position both legs of a patient. FIGS. 6–13 show a preferred embodiment of the apparatus of the present invention designed to position both legs of a patient at various flexion angles. In this embodiment, two leg-engaging trough-shaped portions 20A and 20B, are reversibly connected to an irregular pentagonal-shaped wedge portion 30. The angle of attachment of the leg-engaging portions 20A and 20B to the wedge portion 30 can be varied to accommodate a variety of different hip flexion angles (see, FIGS. 5, 12 and 13).

Figure 6:
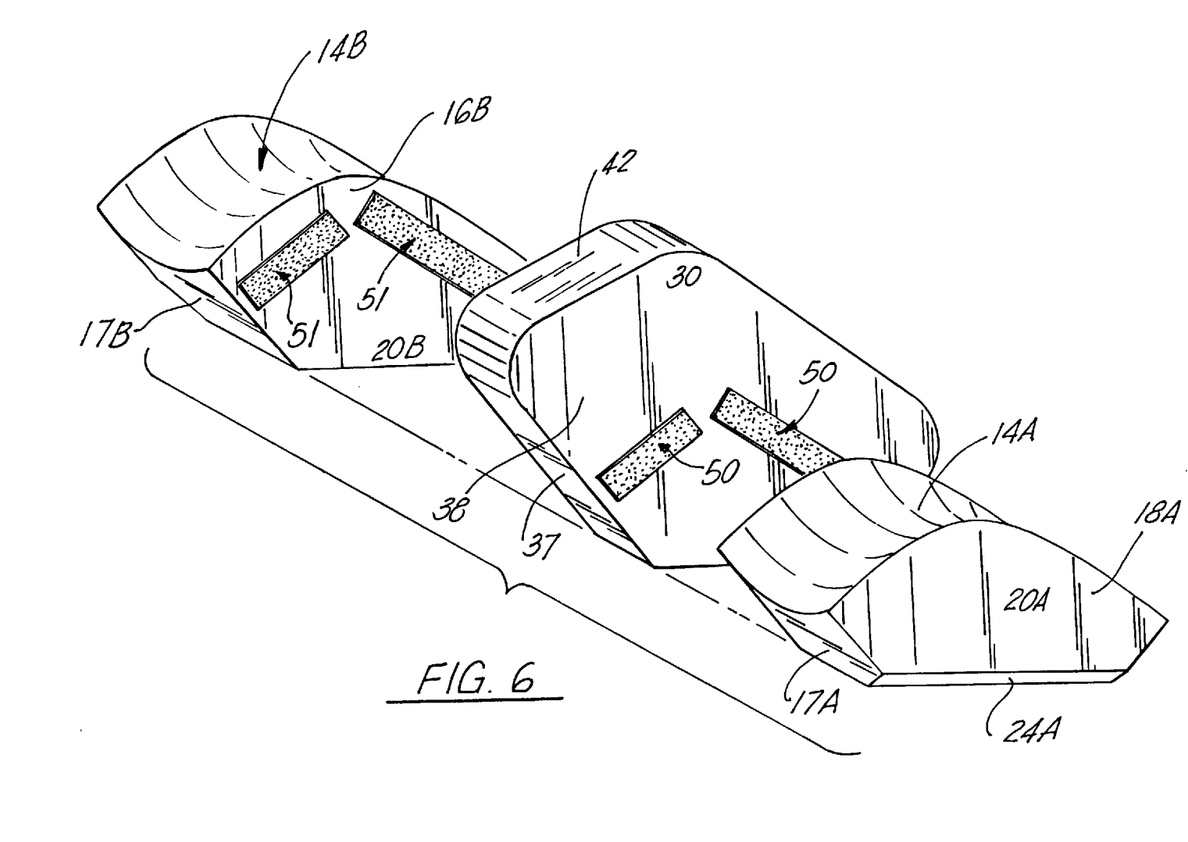
FIG. 6 shows a perspective view of three component pieces of the invention.

FIGS. 6 shows the component parts of this embodiment of the invention just prior to assembly. As can be seen, the first side 38 of a wedge portion 30 is attached to a first side 16 of a first leg-engaging portion 20A, while the second side (not visible) of the wedge portion 30 is attached to the first side 16B of a second leg-engaging portion 20B. The second leg-engaging portion 20B is simply a mirror image of the first leg-engaging portion 20A. The angle of the first and second leg-engaging portions 20A and 20B relative to each other and relative to the wedge 30, can accommodate a variety of different flexion angles (see, FIGS. 5, 12, and 13) and different leg lengths. For example, this device can be used for an amputee.

Figure 7:
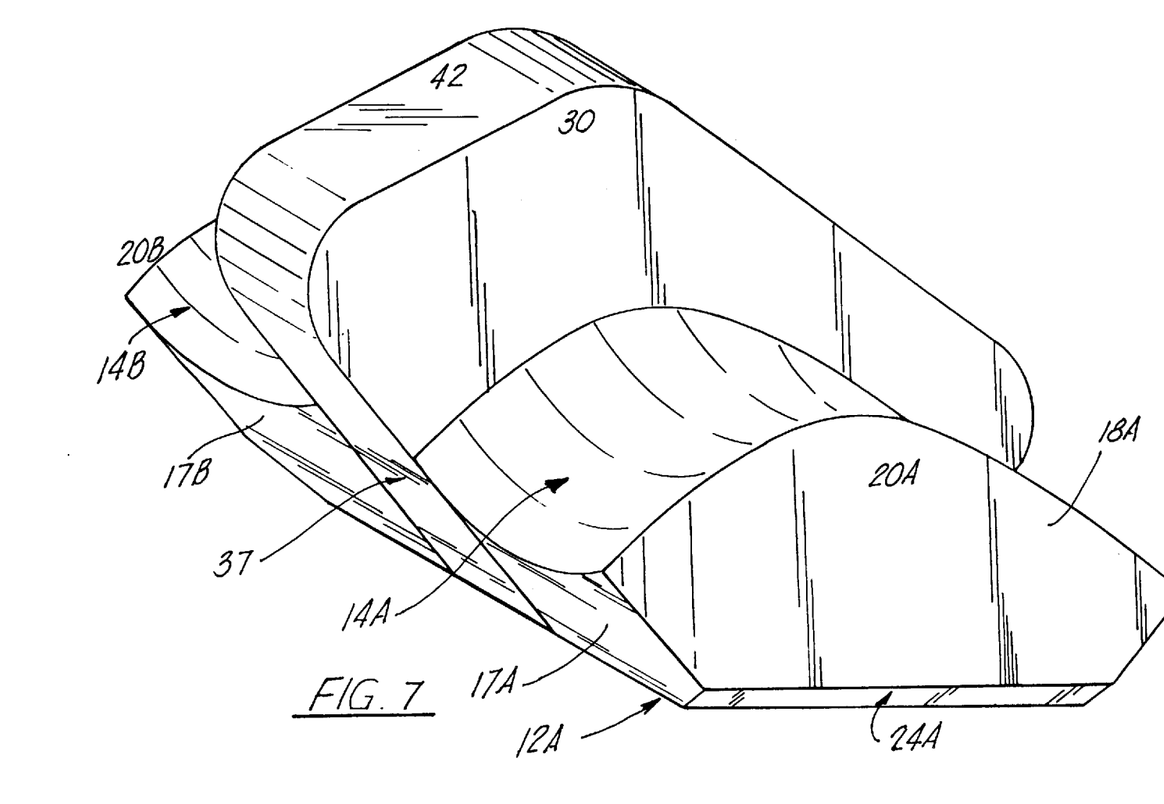
FIG. 7 shows a perspective view of the assembled invention.
Figure 10:
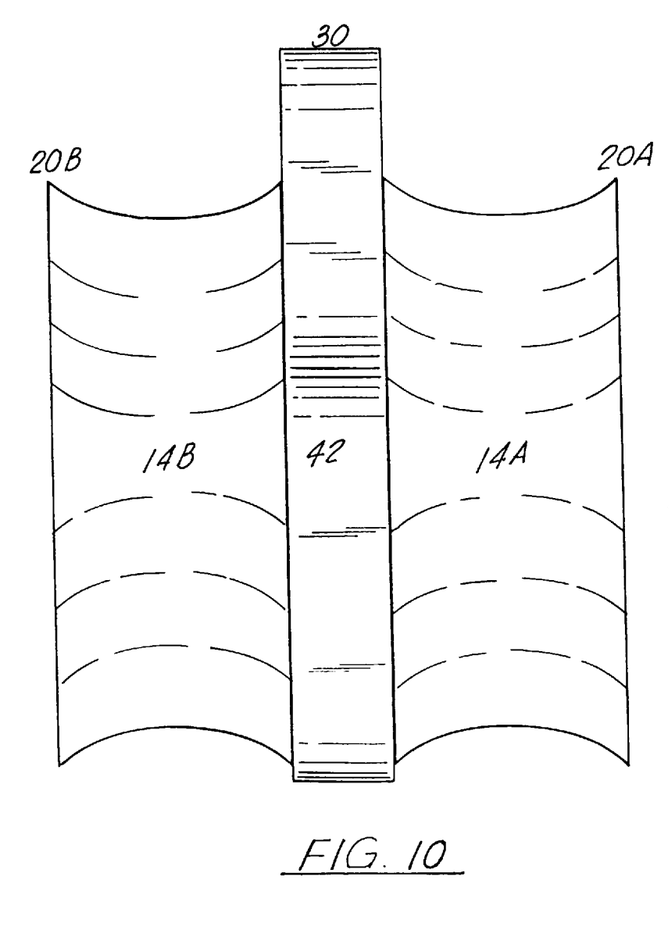
FIG. 10 shows a top perspective view of the assembled invention.
Figure 11:
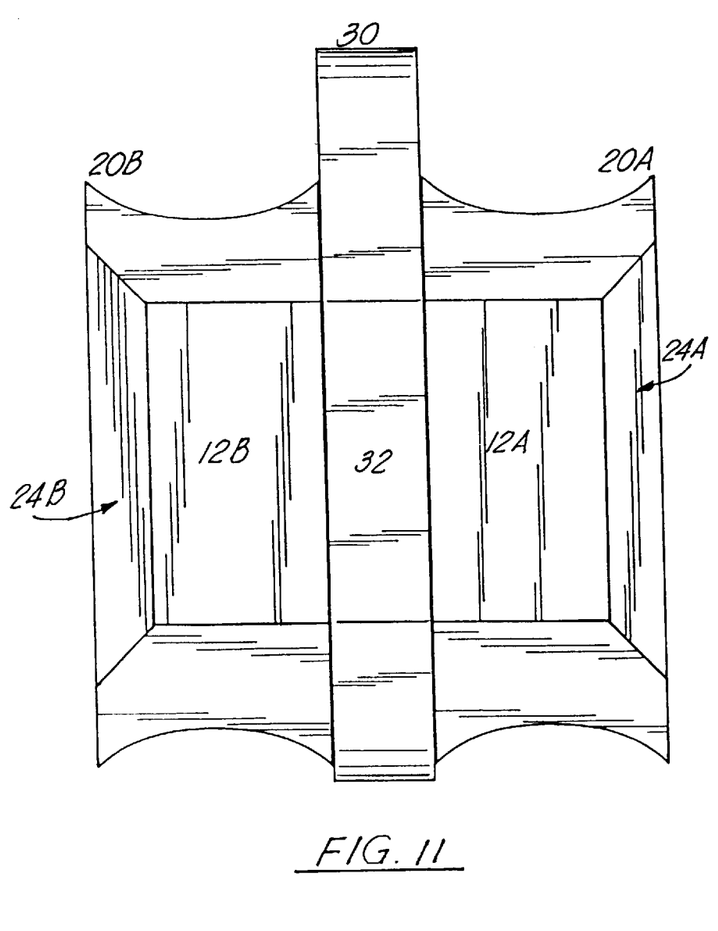
FIG. 11 shows a bottom perspective view of the assembled invention.
Figure 12:
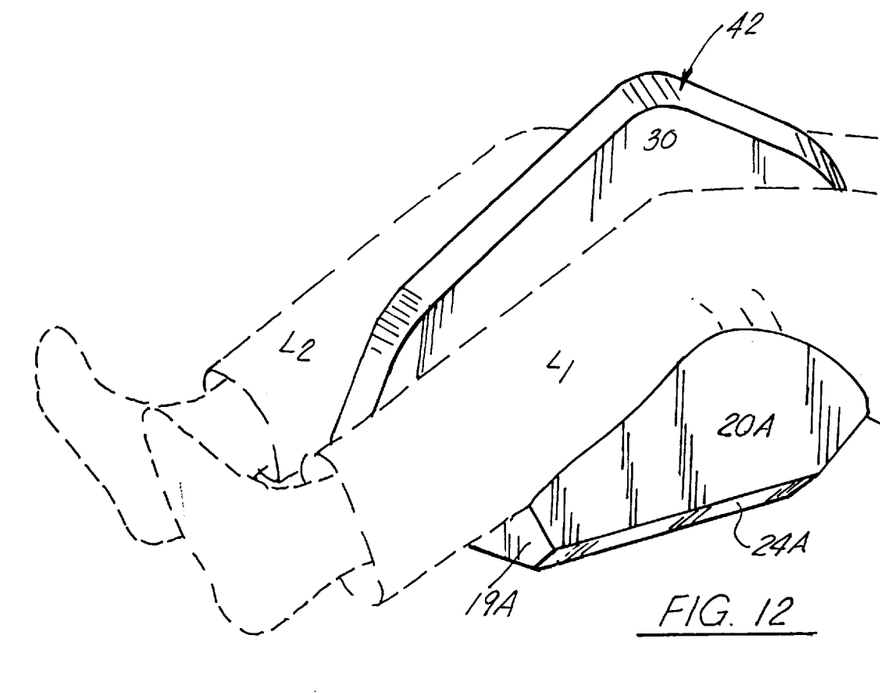
FIG. 12 shows a perspective side view of a patient's legs positioned in the assembled invention.
Figure 13:
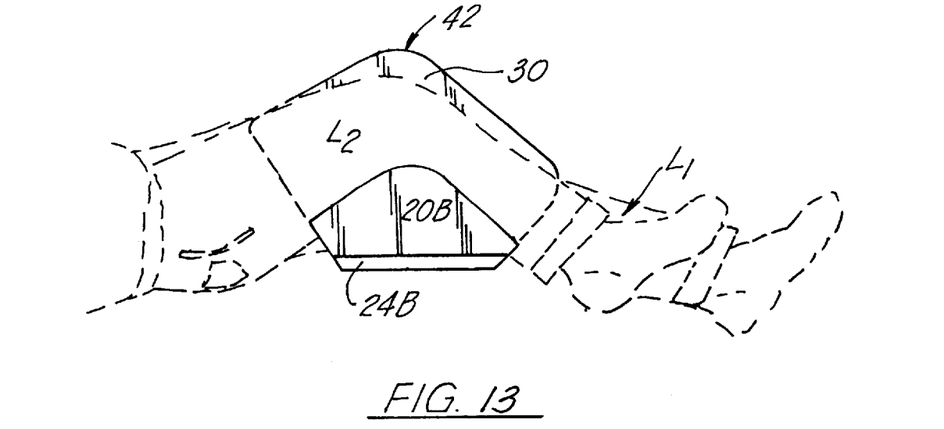
FIG. 13 shows a perspective side view of a patient's legs positioned at different knee flexion angles in the assembled invention.

FIG. 7 shows the embodiment comprising two leg-engaging portions 20A and 20B and a single wedge portion 30 fully assembled. FIGS. 8, and 9 shows a front and back view respectively of this embodiment. The trough-shaped top surfaces 14A and 14B of leg-engaging portions 20A and 20B are shaped to accommodate the thigh and lower leg of a patient as can be seen from the deeper trough at the front of the apparatus compared to the back. However, the size of these troughs as well as their shape can be custom fit to the patient by carving the foam into an appropriate shape. FIGS. 10 and 11 show the top and bottom view, respectively of this same assembled embodiment. Because the bottom surfaces 12A and 12B of the leg-engaging portions 20A and 20B as well as the bottom surface 32 of the wedge portion 30 are all flat, the bottom of the assembled device is also flat. This helps maintain the stability of the foam support while the patient is positioned within it. FIGS. 12 and 13 show the placement of legs L1, and L2 in this embodiment of the invention device. As can be seen, the two legs L1, and L2 can be adjusted to accomodate the same (FIG. 12), or different (FIG. 13) flexion angles relative to each other.

Figure 14:
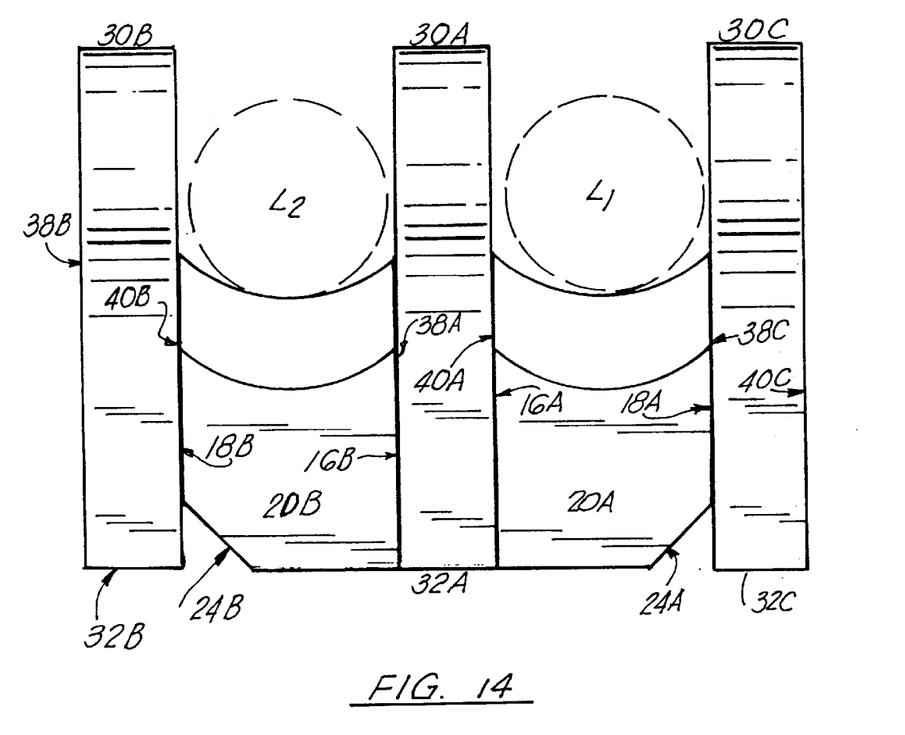
FIG. 14 shows an alternative embodiment of the assembled invention, where three wedge portions are reversible attached to two leg-engaging portions.

Various other alternative embodiments can be accomplished by simply adding or subtracting more or less wedge pieces at different positions. FIG. 14 shows another alternative embodiment of the instant invention. Here, two leg-engaging portions 20A and 20B are attached to three wedge portions 30A, 30B, and 30C. The center wedge portion 30A helps prevent pressure sores due to prolonged leg on leg contact, while the outside wedges 30B and 30C help prevent pressure sores due to prolonged leg on sheet contact, as well as prevent the patient's legs from rolling to a side-lying position.

Other embodiments of the instant invention (not shown) include, but are not limited to, reversibly attaching more than one wedge portion 30 between two leg-engaging portions in order to achieve greater separation of the patient's legs, and attaching more than one wedge portion 30 to either side of a single leg-engaging portion 20 to achieve greater separation of a supported knee from an unsupported knee.

Each component piece of the present invention (e.g. the leg-engaging portion 20, and the wedge portion 30) can be covered with a material such as a washable polyester cover, a sheet, or a pillowcase (not shown). The carvable foam can be wiped clean with a damp cloth. This foam can be fire-retardant open or closed-cell foam.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

We claim:

1. A modular knee positioning support comprising:
   a leg-engaging trough portion having a bottom flat surface, said bottom flat surface having a first straight-edge, and a second angled-edge, a top concave surface, a first side integrally connected to said first straight-edge of said bottom flat surface, and a second side integrally connected to said second angled-edge of said bottom flat surface; and a first wedge portion having a bottom flat surface, a top surface, and a first and second side integrally connecting said bottom flat surface to said top surface;

wherein said first side of said first wedge portion is reversibly connected to said first side of said leg-engaging trough portion.

2. The knee positioning support of claim 1, comprising a second wedge portion, wherein said second side of said second wedge portion is reversibly connected to said second side of said leg-engaging trough portion.

3. The knee positioning support of claim 1, comprising a second wedge portion, wherein said first side of said second wedge portion is reversibly connected to said second side of said first wedge portion.

4. The knee positioning support of claim 3, comprising at least one additional wedge portion, wherein said at least one additional wedge portion is reversibly positioned between said first and second wedge portions.

5. The knee positioning support of claims 1, 2, 3, or 4, wherein said support is constructed from carvable foam.

6. The knee positioning support of claim 5, wherein said foam is fire-retardant open-cell foam.

7. The knee positioning support of claims 1, 2, 3, or 4, wherein said support further comprises a cover positioned over said foam.

8. The knee positioning support of claim 7, wherein said cover is removable.

9. The knee positioning support of claim 7, wherein said cover is selected from the group consisting of a sheet, a pillowcase, and a washable polyester cover.

10. The knee positioning support of claims 1, 2, 3, or 4, wherein said reversible connection is via a hook and loop material.

11. The knee positioning support of claim 1, wherein said removable connection is via hook and loop material.

12. A modular knee positioning support comprising:

first and second leg-engaging trough portions, each having a bottom flat surface, said bottom flat surface having a first straight-edge, and a second angled-edge, a top concave surface, a first side integrally connected to said first straight-edge of said bottom flat surface, and a second side integrally connected to said second angled-edge of said bottom flat surface; and a first wedge portion having a bottom flat surface, a top surface, and a first and second side integrally connecting said bottom flat surface to said top surface;

wherein said first side of said first wedge portion is reversibly connected to said first side of said first leg-engaging trough portion, and said second side of said first wedge portion is reversibly connected to said first side of said second leg-engaging trough portion.

13. The modular knee support device of claim 12, comprising a second wedge portion having a first and second side, wherein said second side of said second wedge portion is reversibly connected to said second side of said first leg-engaging trough portion.

14. The modular knee support device of claim 13, comprising a third wedge portion having a first and second side, wherein said first side of said third wedge portion is reversibly connected to said second side of said second leg-engaging trough portion.

15. A modular knee support device comprising:

first and second leg-engaging trough portions, each having a bottom flat surface, said bottom flat surface having a first straight-edge, and a second angled-edge, a top concave surface, a first side integrally connected to said first straight-edge of said bottom flat surface, and a second side integrally connected to said second angled-edge of said bottom flat surface;

a first and second wedge portion, each wedge having a bottom flat surface, a top surface, and a first and second side integrally connecting said bottom flat surface to said top surface;

wherein said first side of said first wedge portion is reversibly connected to said first side of said leg-engaging trough portion;

said second side of said second wedge portion is reversibly connected to said first side of said second leg-engaging trough portion; and and said second side of said first wedge portion is reversibly connected to said first side of said second wedge portion.

16. The knee positioning support of claim 15, comprising at least one additional wedge portion, said at least one additional wedge portion reversibly positioned between said first and said second wedge portions.

17. The knee positioning support of claim 12, 13, 14, 15, or 16, wherein said support is constructed from carvable foam.

18. The knee positioning support of claim 12, 13, 14, 15, or 16, wherein said foam is fire-retardant open-cell foam.

19. The knee positioning support of claim 17, wherein said support comprises a cover positioned over said foam.

20. The knee positioning support of claim 19, wherein said cover is removable.

21. The knee positioning support of claim 19, wherein said cover is selected from the group consisting of a sheet, a pillowcase, and a washable polyester cover.

* * * * *